US012693544B2

(12) United States Patent
Bo et al.

(10) Patent No.: US 12,693,544 B2
(45) Date of Patent: Jul. 28, 2026

(54) FIELD-OF-VIEW STITCHING SYSTEM AND METHOD, BIOLOGICAL SAMPLE IDENTIFICATION DEVICE AND METHOD

(71) Applicant: MGI Tech Co., Ltd., Shenzhen (CN)

(72) Inventors: En Bo, Shenzhen (CN); Li-Yan Song, Shenzhen (CN); Ang Liu, Shenzhen (CN); Qing-Shan Long, Shenzhen (CN); Sheng-Yuan Zhou, Shenzhen (CN)

(73) Assignee: MGI Tech Co., Ltd., Shenzhen (CN)

( * ) Notice: Subject to any disclaimer, the term of this patent is extended or adjusted under 35 U.S.C. 154(b) by 540 days.

(21) Appl. No.: 18/275,035

(22) PCT Filed: Apr. 30, 2021

(86) PCT No.: PCT/CN2021/091769
§ 371 (c)(1),
(2) Date: Jul. 31, 2023

(87) PCT Pub. No.: WO2022/227091
PCT Pub. Date: Nov. 3, 2022

(65) Prior Publication Data
US 2024/0085715 A1 Mar. 14, 2024

(51) Int. Cl.
*G02B 27/10* (2006.01)
*B01L 3/00* (2006.01)
(Continued)

(52) U.S. Cl.
CPC .... *G02B 27/1066* (2013.01); *B01L 3/502715* (2013.01); *C12Q 1/6869* (2013.01); *G01N 21/6486* (2013.01); *G02B 27/58* (2013.01);

*B01L 2200/025* (2013.01); *B01L 2300/0654* (2013.01); *B01L 2300/168* (2013.01)

(58) Field of Classification Search
CPC ....... B01L 2200/025; B01L 2300/0654; B01L 2300/168; B01L 3/502715; C12Q 1/6837; C12Q 1/6869; G01N 2021/6421; G01N 2021/6463; G01N 21/6458;
(Continued)

(56) References Cited

U.S. PATENT DOCUMENTS

2017/0045744 A1* 2/2017 Amitai ................. G02B 5/3083

FOREIGN PATENT DOCUMENTS

CN 108779976 A * 11/2018 ......... G01B 9/02067

* cited by examiner

*Primary Examiner* — Jennifer Wecker
(74) *Attorney, Agent, or Firm* — ScienBiziP, P.C.

(57) ABSTRACT

A field-of-view stitching system including: a light source module for emitting a first beam; a light guiding element for splitting the first beam into a plurality of second beams and includes an incident surface, a first exit surface, and a plurality of second exit surfaces, the second beams propagate along an optical path of the first beam; and a plurality of light modulators, a number of the plurality of light modulators is the same as a total number of the first exit surface and the plurality of second exit surfaces, each of the plurality of light modulators is configured to receive and regularly reflect one of the plurality of second beams; the light guiding element is further configured to receive and combine the second beams reflected by the light modulators to form an illuminating light. A field-of-view stitching method, a biological sample identification device and method are also provided.

28 Claims, 13 Drawing Sheets

(51) Int. Cl.
   *C12Q 1/6869*          (2018.01)
   *G01N 21/64*          (2006.01)
   *G02B 27/58*          (2006.01)

(58) Field of Classification Search
   CPC .............. G01N 21/6486; G02B 21/361; G02B
                         27/1066; G02B 27/58; G02B 5/04
   See application file for complete search history.

| Number of edges | Regular polygon | Non regular polygon | | | | | |
|---|---|---|---|---|---|---|---|

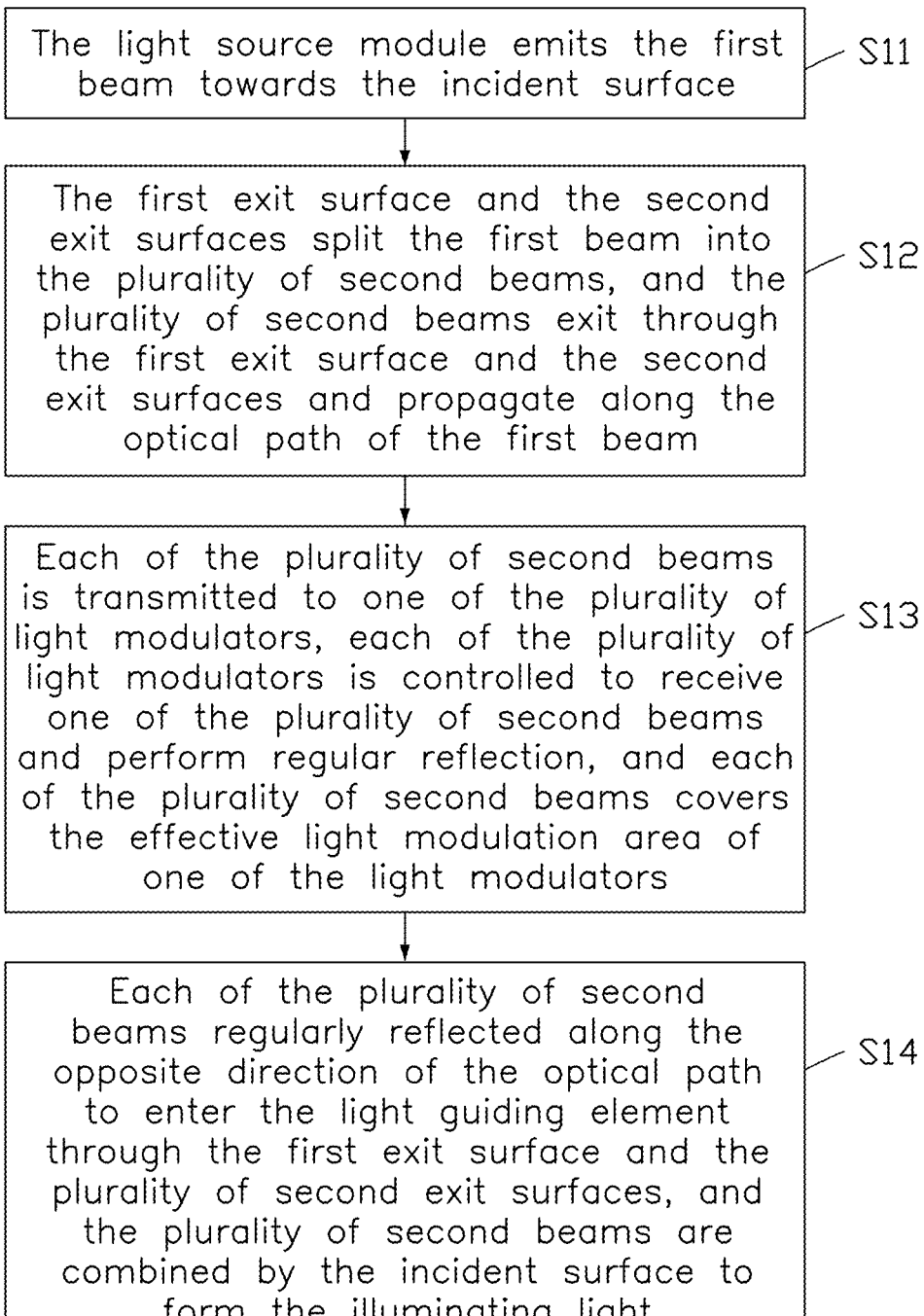

The light source module emits the first beam towards the incident surface — S11

The first exit surface and the second exit surfaces split the first beam into the plurality of second beams, and the plurality of second beams exit through the first exit surface and the second exit surfaces and propagate along the optical path of the first beam — S12

Each of the plurality of second beams is transmitted to one of the plurality of light modulators, each of the plurality of light modulators is controlled to receive one of the plurality of second beams and perform regular reflection, and each of the plurality of second beams covers the effective light modulation area of one of the light modulators — S13

Each of the plurality of second beams regularly reflected along the opposite direction of the optical path to enter the light guiding element through the first exit surface and the plurality of second exit surfaces, and the plurality of second beams are combined by the incident surface to form the illuminating light — S14

FIG. 14

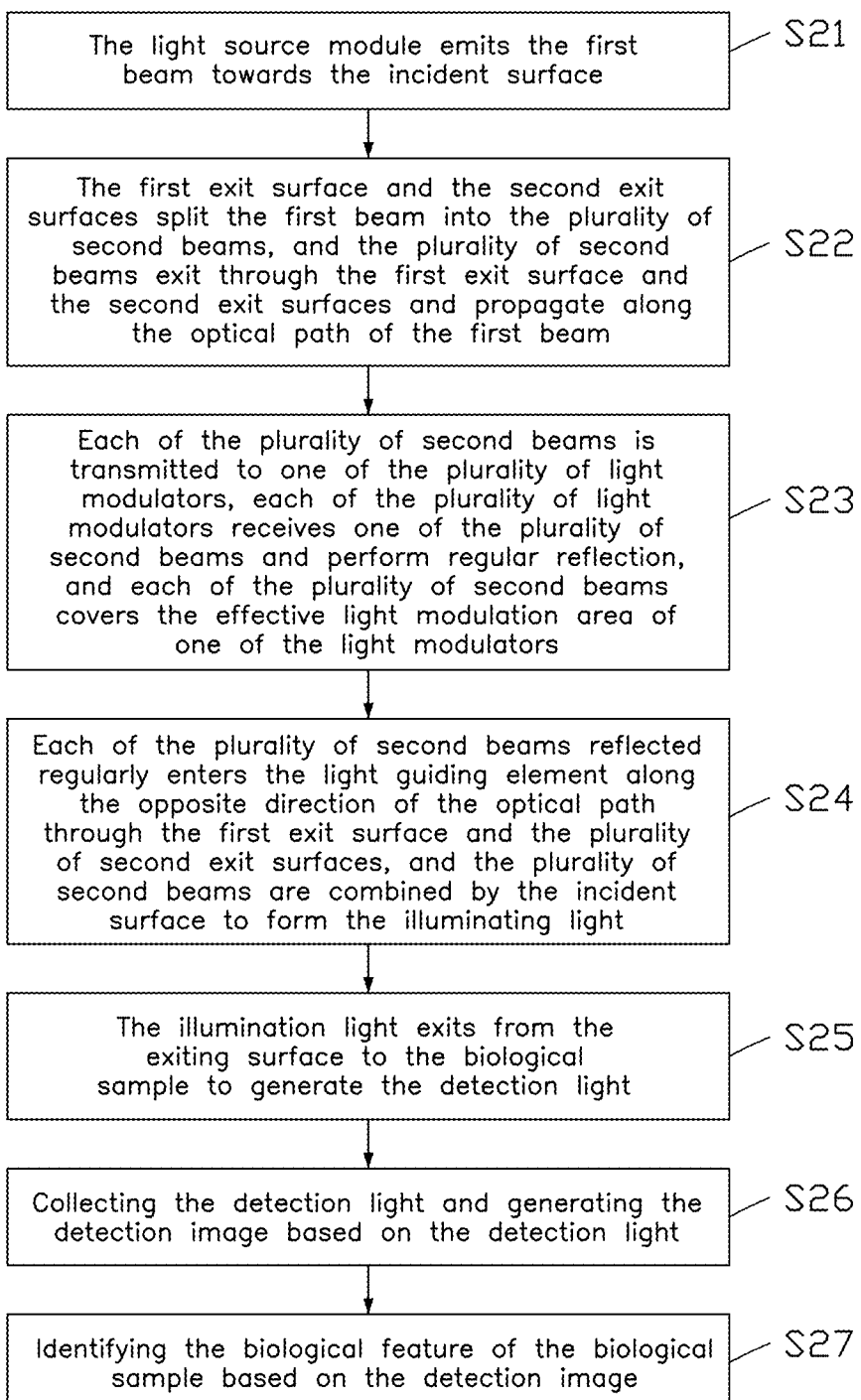

The light source module emits the first beam towards the incident surface — S21

The first exit surface and the second exit surfaces split the first beam into the plurality of second beams, and the plurality of second beams exit through the first exit surface and the second exit surfaces and propagate along the optical path of the first beam — S22

Each of the plurality of second beams is transmitted to one of the plurality of light modulators, each of the plurality of light modulators receives one of the plurality of second beams and perform regular reflection, and each of the plurality of second beams covers the effective light modulation area of one of the light modulators — S23

Each of the plurality of second beams reflected regularly enters the light guiding element along the opposite direction of the optical path through the first exit surface and the plurality of second exit surfaces, and the plurality of second beams are combined by the incident surface to form the illuminating light — S24

The illumination light exits from the exiting surface to the biological sample to generate the detection light — S25

Collecting the detection light and generating the detection image based on the detection light — S26

Identifying the biological feature of the biological sample based on the detection image — S27

FIG. 15

FIELD-OF-VIEW STITCHING SYSTEM AND METHOD, BIOLOGICAL SAMPLE IDENTIFICATION DEVICE AND METHOD

TECHNICAL FIELD

The present disclosure generally relates to optical imaging technology field, particularly relates to a field of view stitching system, a field of view stitching method applied to the field of view stitching system, a biological sample identification device based on super-resolution imaging using the field of view stitching system, and a biological sample identification method based on super-resolution imaging using the biological sample identification device which is based on super-resolution imaging.

BACKGROUND

Gene sequencing refers to analyzing an arrangement sequence of four kinds of bases in a nucleic acid sample. With the rapid development of gene sequencing, super-resolution imaging sequencing systems have emerged for gene sequencing. The super-resolution sequencing system relies on a digital micromirror device (DMD).

The DMD is used to receive illumination light and modulate structured light to project the structured light onto a sequencing chip loaded with nucleic acid samples, which forms a specific structured illumination on a surface of the nucleic acid samples. The super-resolution imaging sequencing system can increase the arrangement density of the nucleic acid samples to be tested each time and can control spaces between nucleic acid samples to be reduced to below 200 nm. The DMD includes a plurality of micro mirrors, and areas of the plurality of micro mirrors determine an array size of the DMD. Due to limitations of the manufacture process of the DMD, the number of the micro mirrors of the DMD and the array size of the DMD both are limited. A traditional super-resolution imaging sequencing system based on the DMD is limited by the array size and the number of the micro mirrors of the DMD, which makes it difficult to expand a field of view of the structured illumination on the nucleic acid samples, and further limits a further improvement of a sequencing throughput.

SUMMARY

A first aspect of the present disclosure provides a field of view stitching system, including:

a light source module for emitting a first beam;

a light guiding element on an optical path of the first beam and configured to split the first beam into a plurality of second beams, wherein the light guiding element includes an incident surface positioned corresponding to the light source module, a first exit surface facing and spaced apart from the incident surface, and a plurality of second exit surfaces bending and extending from edges of the first exit surface towards the incident surface, the plurality of second beams exit from the first exit surface and the plurality of second exit surfaces and propagate along the optical path; and a light modulation module comprising a plurality of light modulators, wherein, a number of the plurality of light modulators is the same as a total number of the first exit surface and the plurality of second exit surfaces, each of the plurality of light modulators is configured to receive and regularly reflect one of the plurality of second beams, each of the plurality of light modulators has an effective light modulation area, each of the plurality of second beams covers the effective light modulation area of one of the light modulators when incident on the light modulator;

wherein the light guiding element is further configured for receiving and combining the plurality of second beams reflected by the plurality of light modulators to form an illuminating light to further exit through the incident surface.

A second aspect of the present disclosure provides a biological sample identification device based on super-resolution imaging, including:

a field of view stitching system, including:

a light source module for emitting a first beam;

a light guiding element on an optical path of the first beam and configured to split the first beam into a plurality of second beams, wherein the light guiding element includes an incident surface positioned corresponding to the light source module, a first exit surface facing and spaced apart from the incident surface, and a plurality of second exit surfaces bending and extending from edges of the first exit surface towards the incident surface, the plurality of second beams exit from the first exit surface and the plurality of second exit surfaces and propagate along the optical path; and a light modulation module including a plurality of light modulators, wherein, a number of the plurality of light modulators is the same as a total number of the first exit surface and the plurality of second exit surfaces, each of the plurality of light modulators is configured to receive and regularly reflect one of the plurality of second beams, each of the plurality of light modulators has an effective light modulation area, each of the plurality of second beams covers the effective light modulation area of one of the light modulators when incident on the light modulator;

wherein the light guiding element is further configured to receive and combine the plurality of second beams reflected by the plurality of light modulators to form an illuminating light to further exit through the incident surface and further configured to irradiate a biological sample to cause a detection light;

an imaging module for receiving the detection light and generating a detection image based on the detection light; and a control portion electrically connected to the light source module, the plurality of light modulators, and the imaging module, the control portion is configured to control an operation process of the light source module, the plurality of light modulators, and the imaging module, and to identify a biological feature of the biological sample based on the detection image.

A third aspect of the present disclosure provides a field of view stitching method applied to a field of view stitching system, wherein the field of view stitching system includes a light source module, a light guiding element, and a light modulation module, the light modulation module is provided with a plurality of light modulators, the light guiding element is provided with an incident surface, a first exit surface facing the incident surface, and a plurality of second exit surfaces bending and extending from edges of the first exit surface towards the incident surface, a number of the plurality of light modulators is the same as a total number of the first exit surface and the plurality of second exit surfaces, and each of the plurality of light modulators has an effective light modulation area; the field of view stitching method comprises:

emitting a first beam towards the incident surface by the light source module;

splitting the first beam into a plurality of second beams by the first exit surface and the plurality of second exit surfaces, and further directing the plurality of second beams to exit from the first exit surface and the plurality of second exit surfaces and propagate along an optical path of the first beam;

transmitting each of the plurality of second beams to one of the plurality of light modulators, controlling each of the plurality of light modulators to receive and regularly reflect one of the plurality of second beams, with each of the plurality of second beams covering the effective light modulation area of the light modulator; and forming an illumination light on the incident surface by a combination of the plurality of second beams which are regularly reflected to the light guiding element along an opposite direction of the optical path and pass through the first exit surface and the plurality of second exit surfaces.

A fourth aspect of the present disclosure provides a biological sample identification method based on super-resolution imaging and is applied to a biological sample identification device, the biological sample identification device is provided with a field of view stitching system including a light source module, a light guiding element, and a light modulation module, the light modulation module includes a plurality of light modulators, the light guiding element is provided with an incident surface positioned corresponding to the light source module, a first exit surface facing and positioned apart from the incident surface, and a plurality of second exit surfaces bending and extending from edges of the first exit surface towards the incident surface, a number of the plurality of light modulators is the same as a total number of the first exit surface and the plurality of second exit surfaces, and each of the plurality of light modulators has an effective light modulation area; the biological sample identification method based on super-resolution imaging comprises:

emitting a first beam towards the incident surface by the light source module;

splitting the first beam into a plurality of second beams by the first exit surface and the plurality of second exit surfaces, and further directing the plurality of second beams to exit from the first exit surface and propagate along an optical path of the first beam;

transmitting each of the plurality of second beams to one of the plurality of light modulators, controlling each of the plurality of light modulators to receive and regularly reflect one of the plurality of second beams, with each of the plurality of second beams covering the effective light modulation area of the light modulator;

forming an illumination light on the incident surface by a combination of the plurality of second beams which are regularly reflected to the light guiding element along an opposite direction of the optical path and pass through the first exit surface and the plurality of second exit surfaces;

irradiating a biological sample with the illumination light through the incident surface to generate a detection light from the biological sample;

collecting the detection light and generating a detection image based on the detection light; and identifying a biological feature of the biological sample based on the detection image.

The field of view stitching system can be applied to various types of optical system. The light guiding element includes the first exit surface and the second exit surface. The light guiding element is configured to split the first beam emitted by the light source module, which makes the first exit surface transmits the second beams, the second exit surface refracts the second beam, therefore each of the second beams can be projected to one of the light modulators in the light modulation module. Each light modulator is used to regularly reflect the received second beam to make the second beams returns back to the light guiding element along an original optical path. That is, each light modulator reflects the second beams with a zero-degree angle with the normal. The light guiding element also is used to collimate the second beams reflected by the light modulators to form the illumination light. The illumination light is formed after modulation by the light modulators, which has a certain shape. Processes based on the light guiding element splitting the first beam and combining the second beams is conducive to stitch the fields of view of the second beams reflected by the light modulators, and obtain the illumination light with a larger field of view, wherein an area of the field of view of the illumination light is the sum of areas of the field of views of all the second beams, thus facilitating usage of a field of view of an objective lens in the optical system of the field of view stitching system.

BRIEF DESCRIPTION OF DRAWINGS

FIG. 5 is a top view of a protrusion portion of the light guiding element in other embodiments.

FIG. 14 is a flow chart of a field of view stitching method of an embodiment.

FIG. 15 is a flow chart of a biological sample identification method based on super-resolution imaging of an embodiment.

DESCRIPTION OF SYMBOLS OF MAIN
COMPONENTS

| | |
|---|---|
| Biological sample identification device | 10 |
| Light source module | 11 |
| Laser device | 111 |
| Beam expanding lens | 112 |
| Light guiding element | 12 |
| Incident surface | 121 |
| First exit surface | 122 |
| Second exit surface | 123 |
| Stage portion | 124 |
| Protrusion portion | 125 |
| Top surface | 126 |
| Bottom surface | 127 |
| Side surface | 128 |
| Inclined plane surface | 129 |
| Light modulation module | 13 |
| Light modulator | 131、DMD1、DMD2、DMD3、 DMD4、DMD5、DMD6、 DMD7、DMD8、DMD9、 |
| Effective light modulation area | 132 |
| Peripheral area | 133 |
| Micro mirror | 134 |
| Substrate | 135 |
| Imaging module | 14 |
| Filter | 141 |
| Camera | 142 |
| Control portion | 15 |
| Total internal reflector | 161 |
| Lens | 162 |
| Dichroic mirror | 163 |
| Objective lens | 164 |
| First beam | L1 |
| Second beam | L2 |
| Illumination light | L3 |
| Detection light | L4 |
| Biological sample | 20 |
| Sequencing chip | 30 |
| Sample platform | 40 |
| Projected area | S0 |
| Projection pattern | S1, S2, S3, S4, S5, S6, S7, S8, S9 |
| Reference plane | P |
| Optic axis | L5 |

The following specific embodiments will further illustrate the present disclosure in conjunction with the above drawings.

DETAILED DESCRIPTION

Embodiment 1

Figure 1:
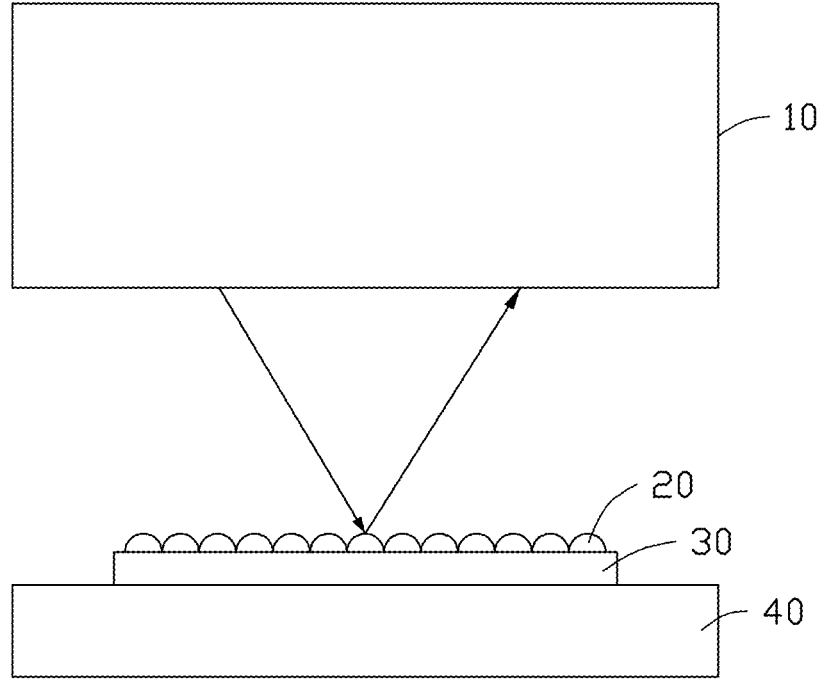
FIG. 1 is a schematic view of a biological sample identification device, a biological sample, a sequencing chip, and a sample platform of an embodiment.

Referring to FIG. 1, a biological sample identification device 10 is used to obtain a biological feature of a biological sample 20. The biological sample 20 may be a nucleic acid sample (DNA or RNA), a protein sample, or a cell sample, etc. In this embodiment, the biological sample 20 is a nucleic acid sample, and the biological feature is a base sequence of the nucleic acid sample.

The biological sample identification device 10 in this embodiment projects laser onto a surface of the biological sample 20 when obtaining the biological feature of the biological sample 20. The biological sample 20 carries a fluorescent labeler, which is stimulated to emit fluorescence when irradiated by the laser. The biological sample identification device 10 is used to receive the fluorescence and generate a detection image based on the fluorescence, and is also used to recognize the detection image to obtain the biological feature of the biological sample 20.

In this embodiment, the biological sample 20 is carried on a sequencing chip 30, and the sequencing chip 30 is carried on a sample platform 40. The biological sample identification device 10 continuously emits the laser during a process of obtaining the biological feature of the biological sample 20, while the sample platform 40 moves horizontally in a plane to drive the sequencing chip 30 and the biological sample 20 to move horizontally in the plane. Therefore, the laser emitted by the biological sample identification device 10 can be projected to different positions on the surface of the biological sample 20. The process of the laser projecting onto different positions on the surface of the biological sample 20 can also be referred as laser scanning of the biological sample 20. In other embodiments, the sample platform 40 may be omitted, while an emission angle of the laser can be changed so that the laser can be projected onto different positions of the biological sample 20.

Figure 2:
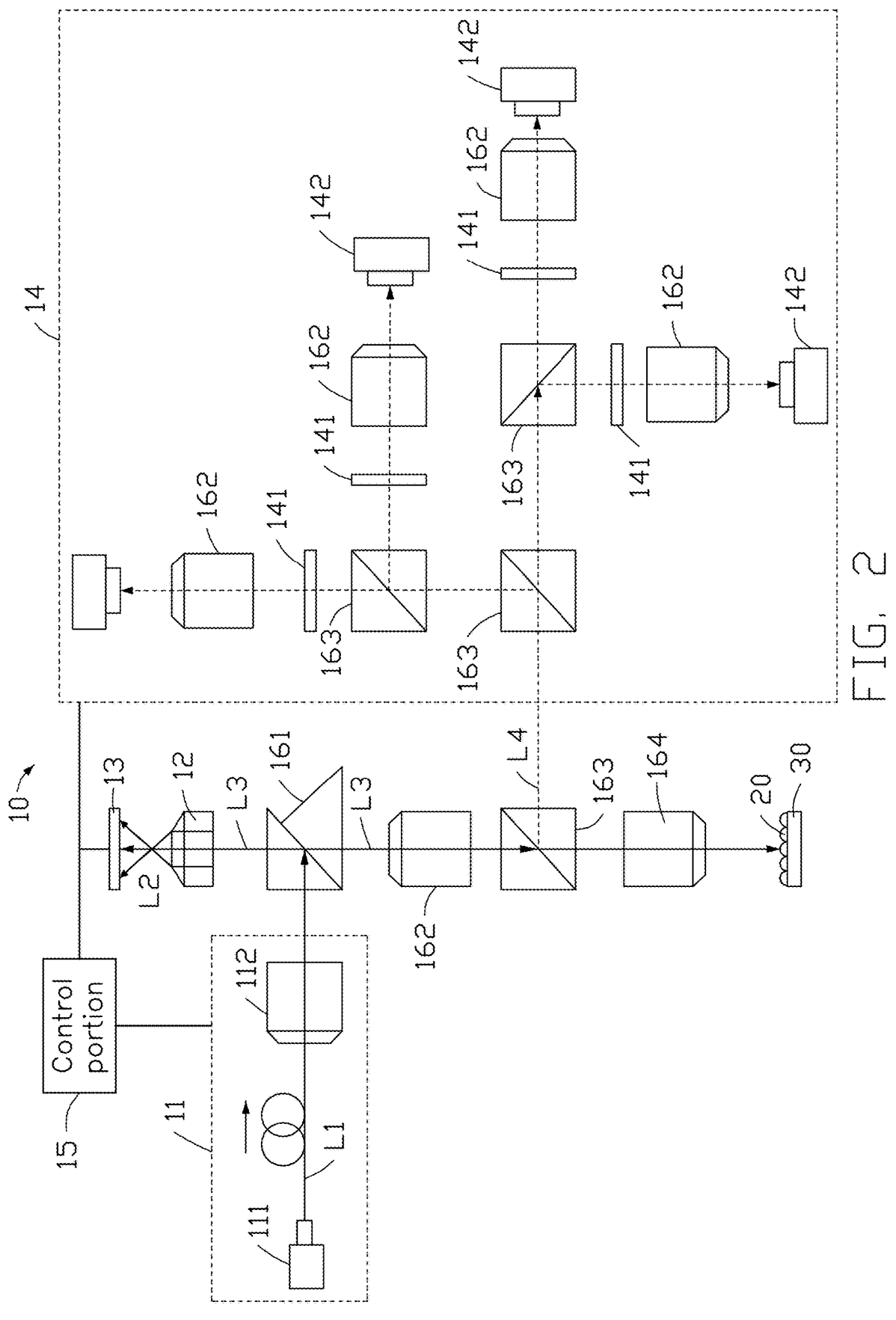
FIG. 2 is a schematic view of an optical path formed by the biological sample identification device, the biological sample, and the sequencing chip in FIG. 1.

Referring to FIG. 2, the biological sample identification device 10 includes a light source module 11, a light guiding element 12, a light modulation module 13, an imaging module 14, and a control portion 15. The light source module 11, the light modulation module 13, and the imaging module 14 are electrically connected to the control portion 15.

In this embodiment, the light source module 11 includes one laser device 111 and a beam expanding lens 112. The laser device 111 is used to emit a first beam L1, which is laser light. The beam expanding lens 112 is on an optical path of the first beam L1 and is used to expand and collimate the first beam L1 transmitted thereto. In other embodiments, the light source module 11 may include other numbers of laser devices, such as two, four, etc. If a spot area of the first beam L1 emitted by the laser device 111 in the light source module 11 meets requirements of a subsequent optical path, the light source module 11 may also not include the beam expanding lens 112.

The light guiding element 12 is on the optical path of the first beam L1 and is used to split the first beam L1 to generate a plurality of second beams L2.

Figure 3:
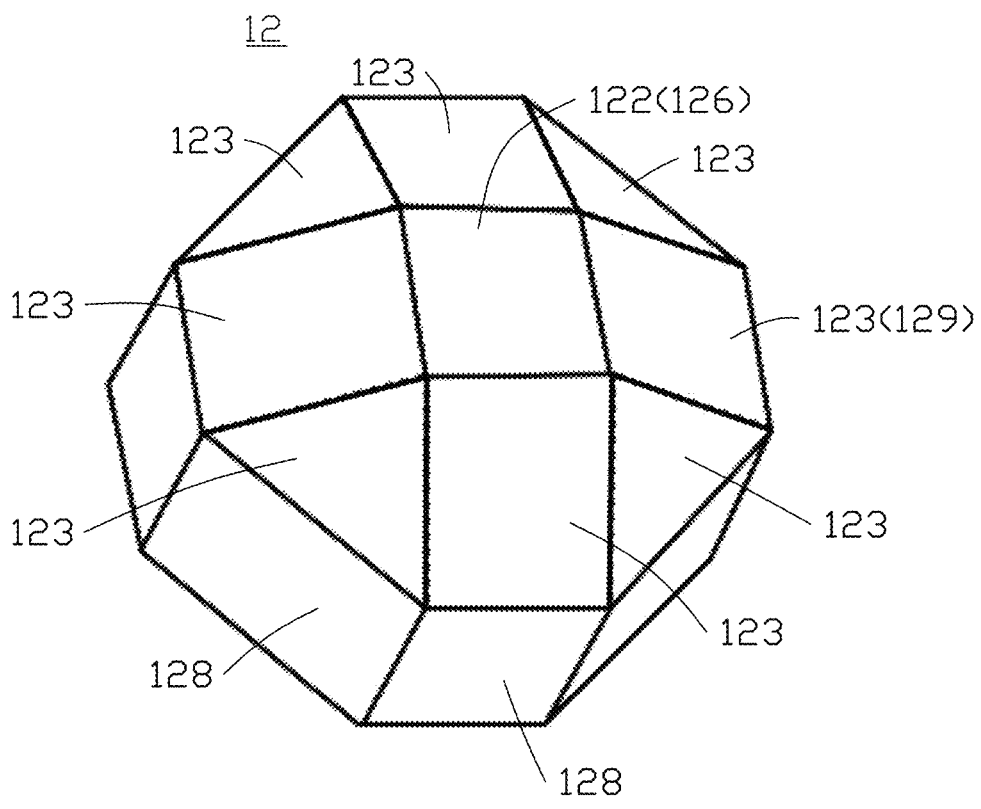
FIG. 3 is a perspective view of a three-dimensional structure of a light guiding element in FIG. 2.
Figure 4:
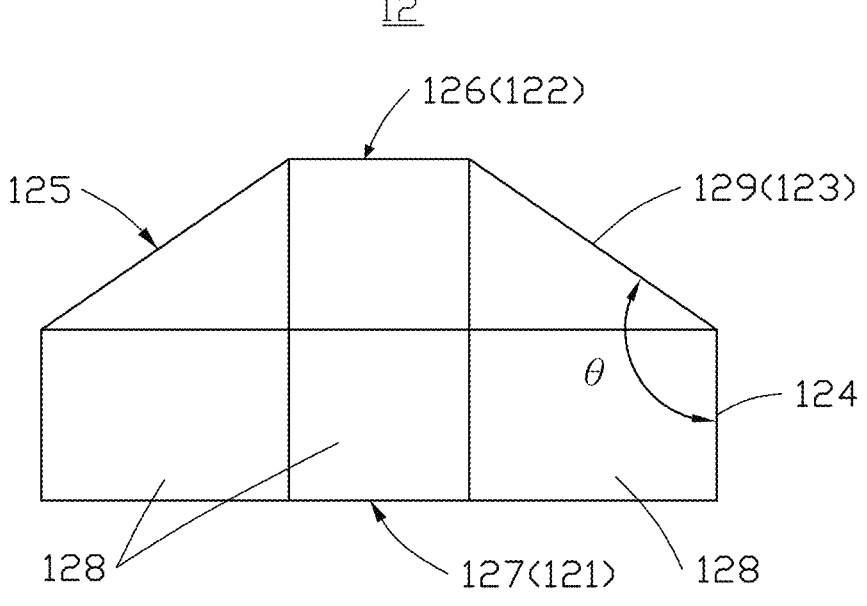
FIG. 4 is a front side view of the light guiding element in other embodiments.

Referring to FIGS. 3 and 4, the light guiding element 12 includes an incident surface 121 positioned corresponding to the light source module 11 for receiving the first beam L1, a first exit surface 122 facing and spaced apart from the incident surface 121, and multiple second exit surfaces 123 bending from edges of the first exit surface 122 and extending towards the incident surface 121. In this embodiment, the first exit surface 122 and the second exit surfaces 123 are interconnected. The second exit surfaces 123 surround the first exit surface 122.

The second beams L2 exit from the first exit surface 122 and the second exit surfaces 123. In this embodiment, one of the second beams L2 is transmitted through the first exit surface 122, and the other second beams L2 are refracted through the second exit surface 123.

In this embodiment, the light guiding element 12 includes one first exit surface 122 and eight second exit surfaces 123, and the light guiding element 12 is used to split the first beam L1 into nine second beam L2. The eight second exit surfaces 123 are interconnected and surround the first exit surface 122. One of the nine second beams L2 directly transmits from the first exit surface 122, while the other eight second beams L2 are refracted by the second exit surfaces 123, respectively.

Figure 5:
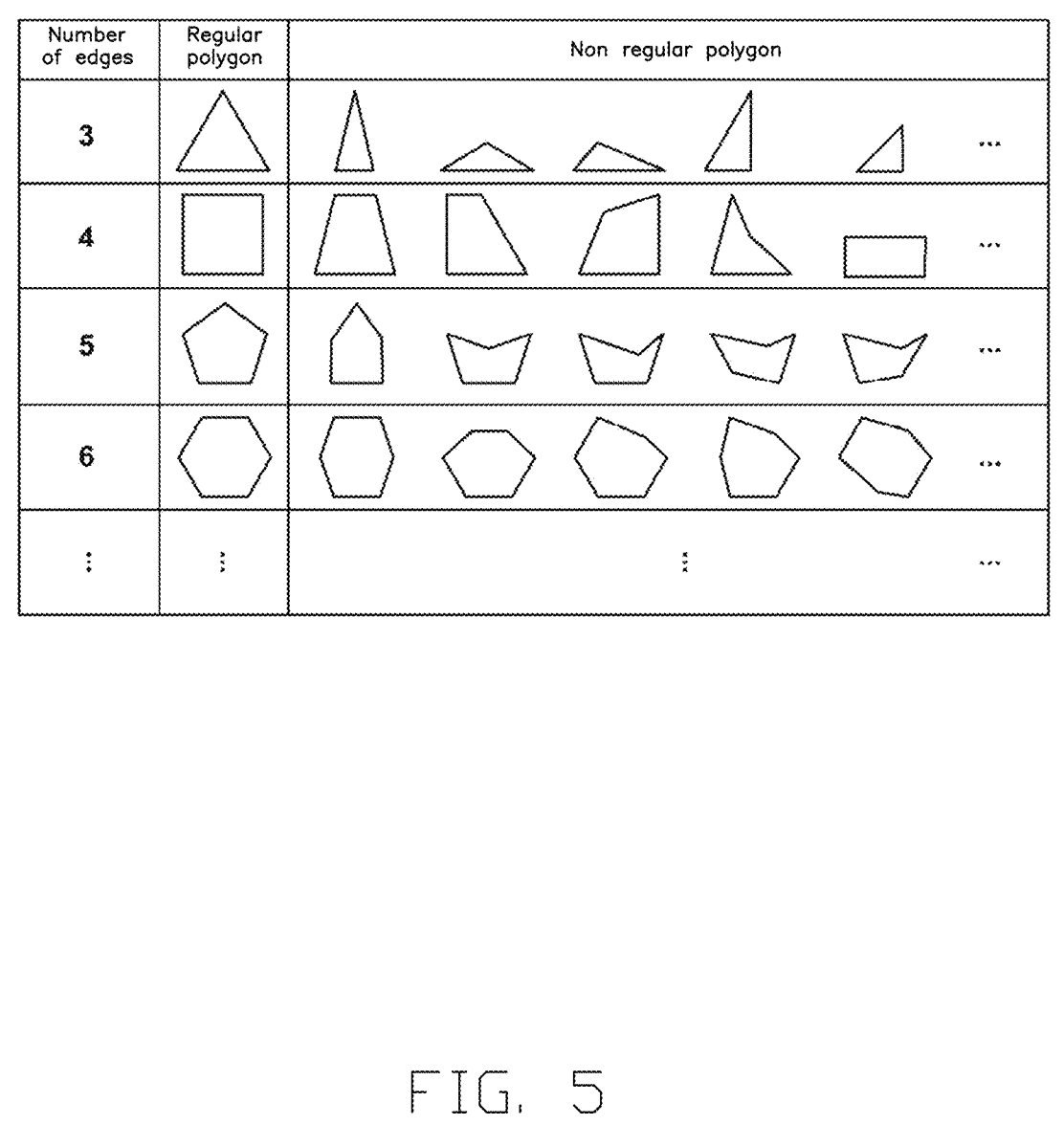
Figure 6:
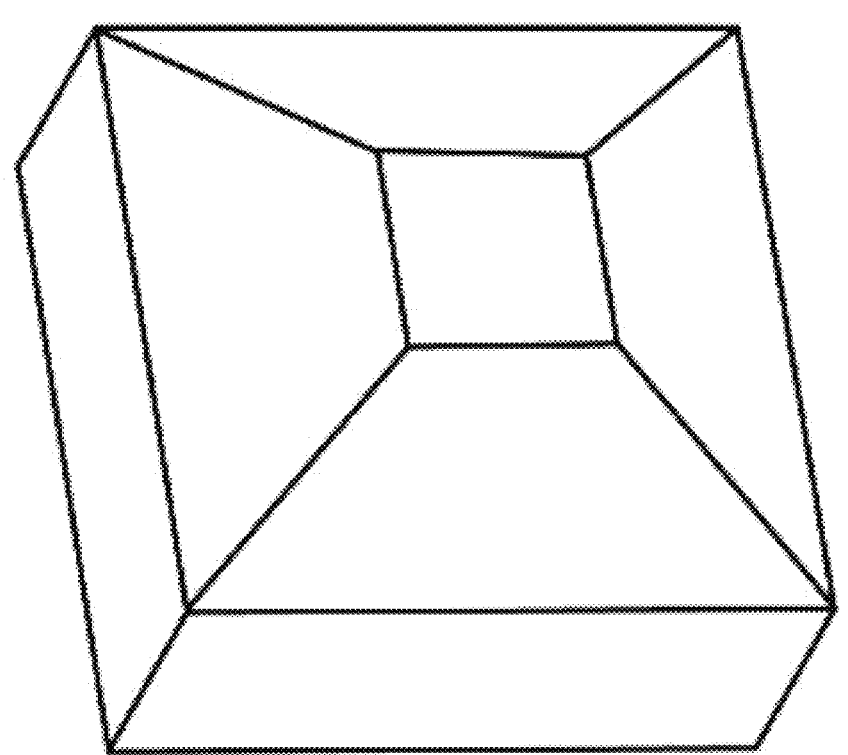
FIG. 6 is a perspective view of another embodiment of the light guiding element in FIG. 2.

The light guiding element 12 of this embodiment is boss-shaped and includes a stage portion 124 and a protrusion portion 125. The stage portion 124 is in shape of a polygonal prism, and the protrusion portion 125 is connected to an end of the stage portion 124 and coaxial with the stage portion 124. The stage portion 124 includes a bottom surface 127 at an end away from the protrusion portion 125 and a plurality of side surfaces 128 between the bottom surface 127 and the protrusion portion 125. The bottom surface 127 is the incident surface 121 of the light guiding element 12. The protrusion portion 125 includes a plurality of inclined plane surfaces 129 and a top surface 126. The inclined plane surfaces 129 are between the top surface 126 and the stage portion 124, each inclined plane surface 129 intersects and is connected with one side surface 128 (an angle θ between the inclined plane surface 129 and the side surface 128 is less than 180°), and each inclined plane surface 129 intersects and connects with the top plane 126. In this embodiment, the top surface 126 is parallel to the bottom surface 127, and an area of the top surface 126 is smaller than an area of the bottom surface 127. The inclined plane surfaces 129 and the top surface 126 cooperatively form the surface of the protrusion portion 125. Each inclined plane surface 129 is one of the second exit surfaces 123, and the top surface 126 is the first exit surface 122. A shape of the top surface 126 (that is, the first exit surface 122) can be the same as or different from the bottom surface 127. For example, the number of edges of the top surface 126 (that is, the first exit surface 122) may be less than the number of edges of the bottom surface 127. In this embodiment, the stage portion 124 is an octagonal prism, the bottom surface 127 (that is, the incident surface 121) is octagonal and has eight sides, the top surface 126 (that is, the first incident surface 122) is quadrilateral and has four sides, the number of the inclined plane surfaces 129 (that is, the second incident surface 123) is the same as the number of edges of the stage portion 124, which is eight, wherein four of the inclined plane surfaces 129 are rectangular (including the case that some of the plane surfaces 129 are square-shaped), the other four of the inclined plane surfaces 129 are triangular, and each second exit surfaces 123 in the shape of a rectangle alternates with one second exit surfaces 123 in the shape of a triangle. Each rectangle-shaped second exit surface 123 is defined as a first refraction surface, and each first refraction surface corresponds to one edge of the first exit surface 122. Each triangle-shaped second exit surface 123 is defined as a second refraction surface, and each second refraction surface corresponds to one corner of the first exit surface 122. In other embodiments, the top surface 126 (that is, the first exit surface 122) can also be in other shapes as shown in FIG. 5. If the number of edges of the first exit surface 122 is represented as M and the number of edges of the stage portion 124 is represented as N, there are two relationships between M and N: (1) N=2M (as shown in FIG. 3); (2) N=M (as shown in FIG. 6).

The nine second beams L2 emitted from the first exit surface 122 and the second exit surfaces 123 of the light guiding element 12 are projected onto a surface of the light modulation module 13 facing the light guiding element 12 (as shown in FIG. 2).

Figure 7:
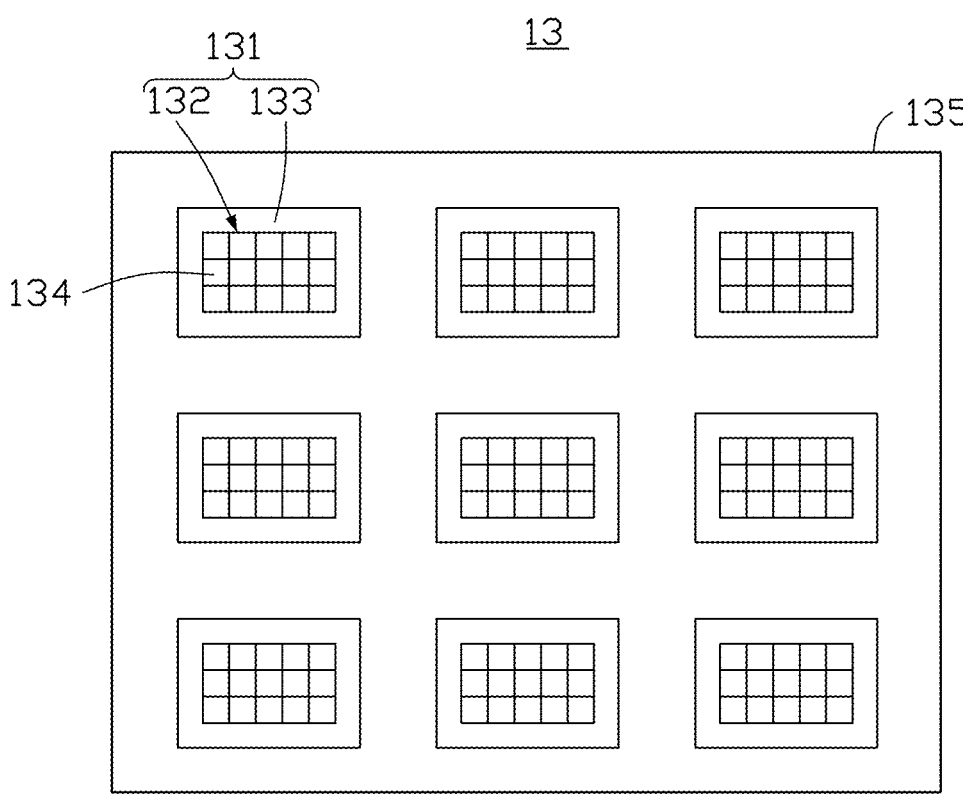
FIG. 7 is a planar view of a light modulation module with multiple micro mirrors in FIG. 2.

Referring to FIG. 7, the light modulation module 13 includes a plurality of light modulators 131 spaced apart from each other. The number of the light modulators 131 is the same as the number of the second beams L2, and each light modulator 131 is used to receive and regularly reflect one of the second beams L2. That is, each light modulator 131 reflects the second beams L2 with a zero-degree angle with the normal. In this embodiment, nine light modulators 131 are included since there are nine second beams L2. The nine light modulators 131 are arranged in an array with three rows and three columns, spaces between any adjacent two light modulators 131 in each row are equal, and spaces between any adjacent two light modulators 131 in each column are equal. Each light modulator 131 includes an effective light modulation area 132 and a peripheral area 133. The peripheral area 133 surrounds and is connected to the effective light modulation area 132. The effective light modulation area 132 is configured for receiving and reflecting the second beams, and the peripheral area 133 is typically used to carry some necessary structures such as peripheral circuits. The light modulation module 13 also includes a substrate 135, and all the light modulators 131 are carried on a same surface of the substrate 135.

In this embodiment, each light modulator 131 is a digital micromirror device (DMD). Each light modulator 131 includes a plurality of micro mirrors 134 in the effective light modulation area 132. The micro mirrors 134 are arranged in an array including a plurality of rows and columns. In other embodiments, each light modulator 131 may be a spatial light modulator.

Figure 8:
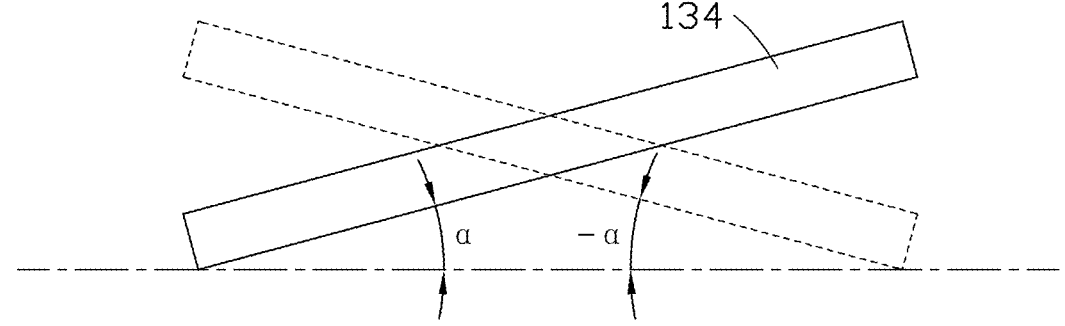
FIG. 8 shows rotation states of the micro mirrors in FIG. 7.

Referring to FIG. 8, each micro mirror 134 can be rotated within a certain angle range. In this embodiment, each micro mirror 134 can be rotated about its axis in two opposite directions, and maximum rotation angles in the two opposite directions are the same. The maximum rotation angles in the two opposite directions are defined as α and −α. When the biological sample identification device 10 is in operation, each micro mirror 134 is controlled to be in a state of rotating an angle α or rotating an angle −α. For each micro mirror 134, a state that the rotation angle of the micro mirror 134 is α is defined as a "ON" state, and a state that the rotation angle of the micro mirror 134 is −α is defined as a "OFF" state.

By adjusting the state of each micro mirror 134 in each light modulator 131, the second beams L2 reflected by the light modulators 131 can be modulated into different shapes, so that the nine second beams L2 are combined by the light guiding elements 12 to form illumination light L3 of different shapes and exit through the incident surface 121. In this embodiment, the illumination light L3 is stripe-shaped, which can also be called stripe structured light. A shape of the illumination light L3 is usually determined by a spot shape formed when the illumination light L3 reaching a surface of the biological sample 20. For example, in this embodiment, the illumination light L3 (that is, stripe structured light) has a stripe pattern, which means the light spot formed on the surface of the biological sample 20 when the illumination light L3 reaching the surface of the biological sample 20 is a stripe pattern.

In this embodiment, parameters of the light guiding element 12 and the light modulation modules 13 need to meet the specific conditions, so that each of the nine second beams L2 from the light guiding element 12 covers the effective light modulation area 132 of one of the light modulators 131, and each light modulator 131 can regularly reflect the second beam L2 transmitted thereto.

The specific conditions include that the light spot formed when each second beam L2 reaching the light modulator 131 can completely cover the effective light modulation area 132 of the light modulator 131.

The specific conditions also include that the second beams L2 projected into the effective light modulation area 132 are regularly reflected by the light modulators 131.

Specific structures of the light guiding element 12 and the light modulation modules 13 in this embodiment will be explained as examples.

Figure 9:
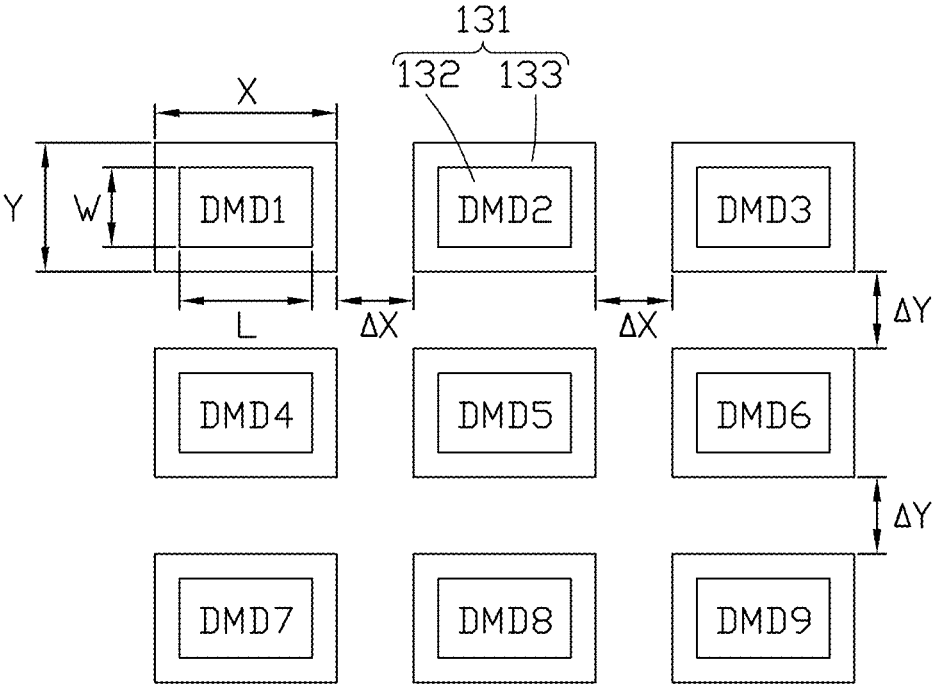
FIG. 9 is another planar view of the light modulation module in FIG. 2.

In this embodiment, N=2M=8. Referring to FIG. 9, the light modulation module 13 includes nine light modulators 131 (represented as DMD1, DMD2, DMD3, DMD4, DMD5, DMD6, DMD7, DMD8, and DMD9, respectively in FIG. 9). The effective light modulation area of each light modulator 131 is rectangular with a length L and a width W. A shape of each light modulator 131 (that is, a contour of the peripheral area 133) is in a rectangle shape with a length X and a width Y. In the array of nine light modulators 131, spaces between any adjacent two light modulators 131 in each row are $\Delta X$, and spaces between any adjacent two light modulators 131 in each column are $\Delta Y$. Referring to FIG. 2, a light outlet of the laser device 111 is rectangular, and the first beam L1 emitted by the laser device 111 can form a rectangular spot with an area of 3 L×3 W (that is, a sum of the effective light modulation areas 132 of the nine light modulators 131) after being expanded and collimated by the beam expanding lens.

The light guiding element 12 splits the first beam L1 along two dimensions: the X dimension and the Y dimension.

Light Splitting in the Y dimension can be described as follows.

Figure 10:
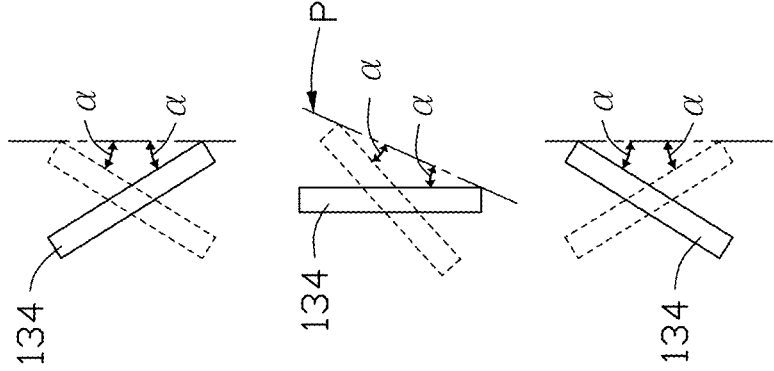
FIG. 10 shows a light-splitting process of the light guiding element in FIG. 2 in a Y dimension.
Figure 10:
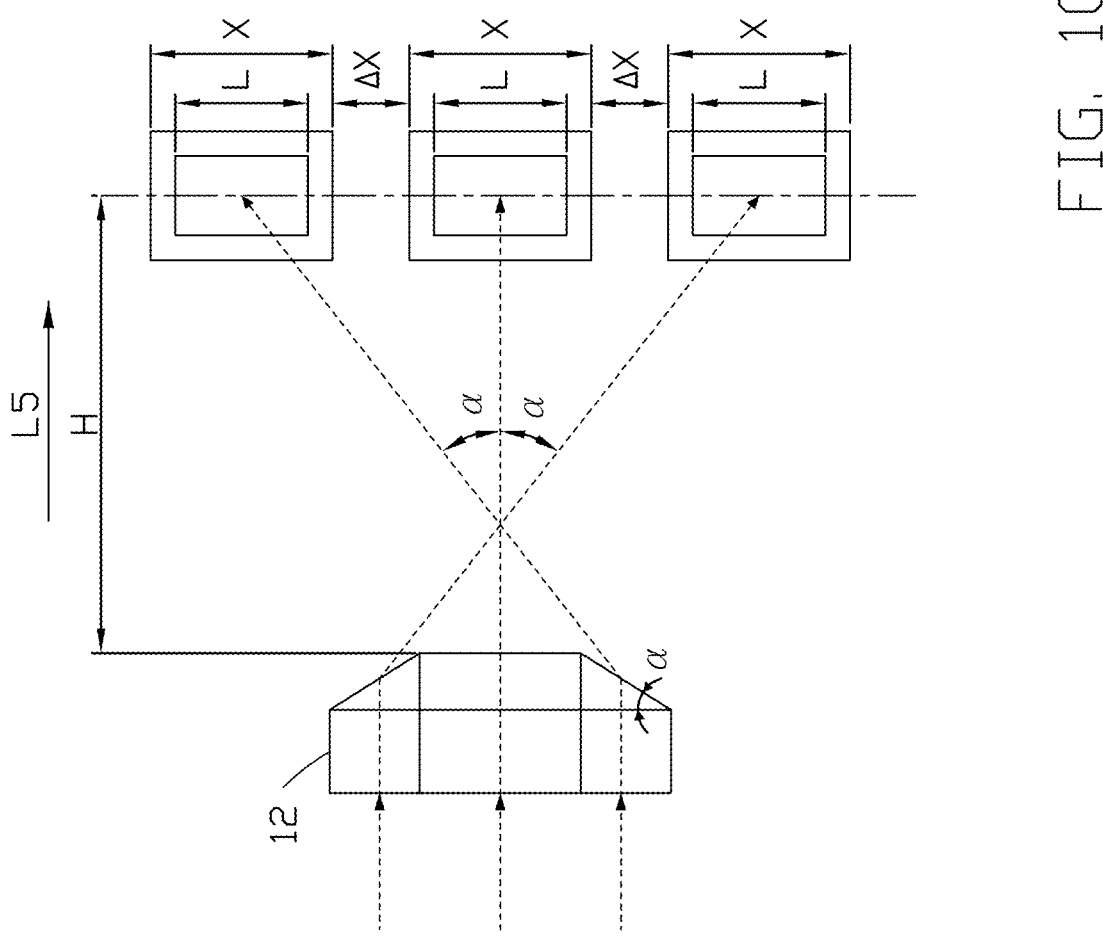

Referring to FIG. 10, in the Y dimension, a size of the first beam L1 is 3 L. A direction in which the light guiding element 12 transmits the second beams L2 is defined as a transmission direction. On a plane formed by the transmission direction and the X direction, a cone angle $\alpha$ is formed by the second exit surfaces 122 and the incident surface 121. A refractive index of the light guiding element 12 is n. The transmission direction of the second beams L2 transmitted from the first exit surface 122 is parallel to an optic axis L5. Along a direction of the optic axis L5, a distance between the light guiding element 12 and the light modulation module 13 is H. If following condition (1) is satisfied, the second beams L2 split along the Y direction can be projected onto corresponding DMD.

$$2H \tan[\alpha(n-1)]=2X+2\Delta X+L \qquad (1)$$

The angle of the DMD can be further adjusted to ensure that the corresponding DMD can regularly reflected the corresponding second beam L2. That is, a surface of each DMD reflecting the second beam L2 is perpendicular to a reflection direction thereof. The light guiding element 12 is on the plane formed of the transmission direction and the X direction, and a cone angle of the second exit surface 123 and the incident surface 121 is equal to the rotation angle of the DMD. Each DMD for receiving and reflecting the second beam L2 transmitted from the first exit surface 121 has a reference plane P, and the micro mirrors 134 maintain an angle $\alpha$ with the reference plane P in both "ON" state and "OFF" state. In this embodiment, the reference plane P of each DMD needs to be rotated with angle $\alpha$ to ensure the second beams L2 received are regularly reflected, which can also meet the condition (1) above.

Light splitting in the X dimension can be described as follows.

Figure 11:
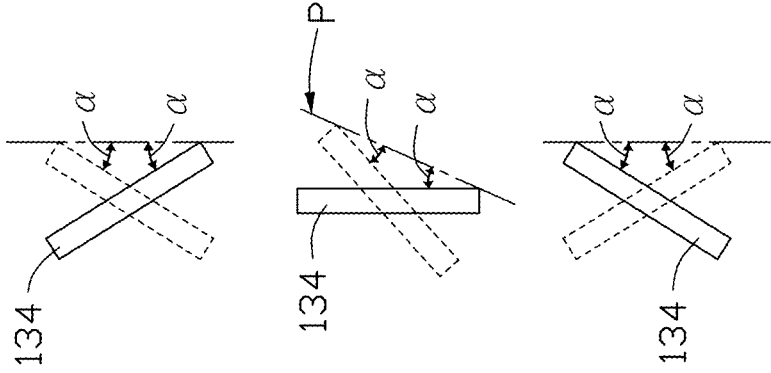
FIG. 11 shows a light-splitting process of the light guiding element in FIG. 2 in an X dimension.
Figure 11:
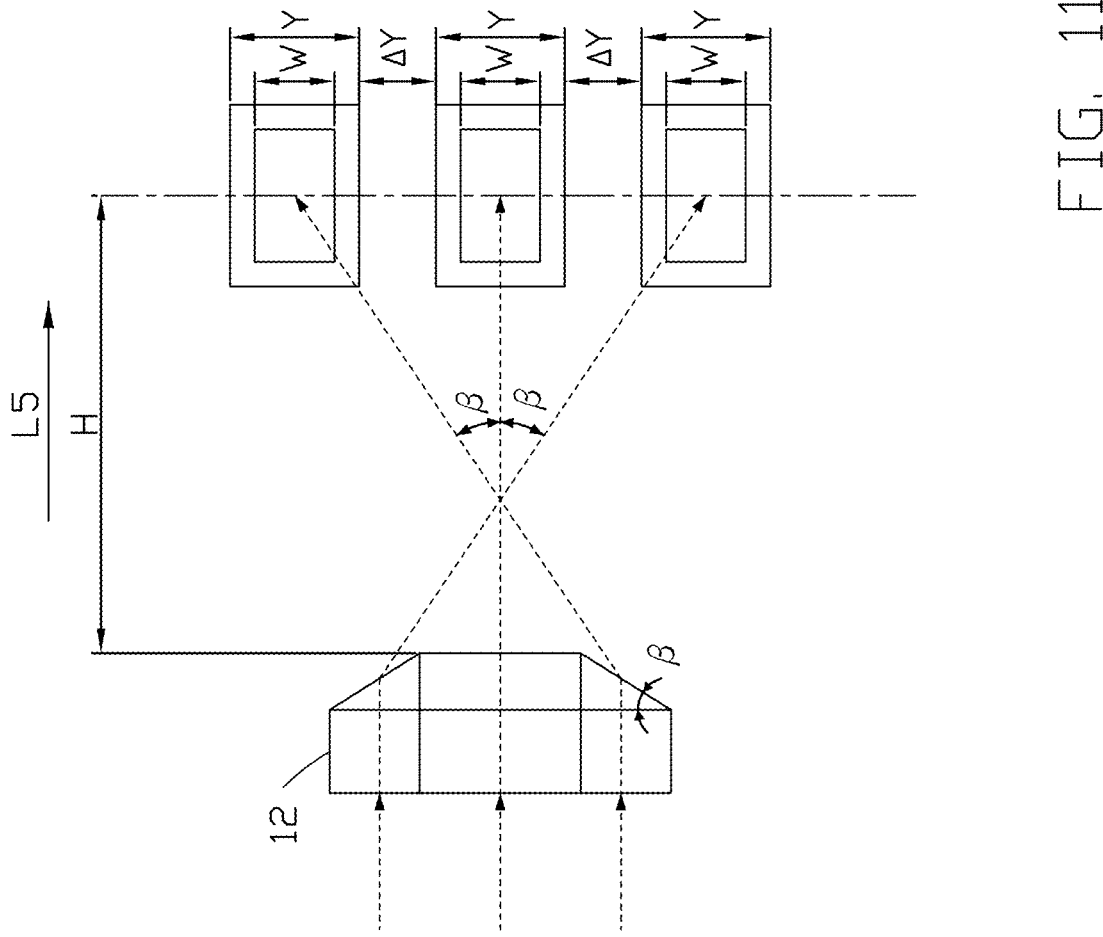

Referring to FIG. 11, in the X dimension, the size of the first beam L1 is 3 W, and the light guiding element 12 is on the plane formed by the transmission direction and the Y direction, a cone angle between the second exit surface 123 and the incident surface 121 is $\beta$. Under a premise of condition (1), a proper distance H can be obtained. Further adjusting the cone angle $\beta$ and the spacing $\Delta Y$ can satisfy the following condition (2), so that the second beams L2 split along the X direction can be projected onto the corresponding DMDs respectively, that is, the condition (2) can be satisfied.

$$2H \tan[\beta(n-1)]=2Y+2\Delta Y+W \qquad (2)$$

Further adjusting the angle of the DMD can ensure that the DMD receiving the second beam L2 split along the X direction can reflect the corresponding second beam L2 regularly, as the cone angle is $\beta$, the rotation angle of the DMD remains $\alpha$, it is necessary to rotate the reference plane P of the DMD to ensure regular reflection. The reference planes P of all the DMDs rotate clockwise with an angle of $\alpha$-$\beta$, and the above condition (2) can be satisfied. The reference plane P of the DMD facing the first reflecting surface 121 has rotated in the Y dimension with the angle $\alpha$, and therefore a total rotation angle is $2\alpha$-$\beta$, which makes it possible to meet condition (2) in the X dimension as well.

Therefore, based on $\Delta X$ and $\Delta Y$, an arrangement of the light modulators 131 in the light modulation module 13 can be determined. Furthermore, based on symmetry characteristics and the cone angles $\alpha$ and $\beta$ of the DMDs in the X direction and the Y direction, a structure of an exit surface (including first exit surface 122, and second exit surface 123) of the light guiding element 12 emitting the second beams L2 can be obtained.

In other embodiments of the present disclosure, for the light modulation module 13 formed by light modulators 131 in other irregularly arrangement, the output surface of the light guiding element 12 can be designed in a shape different from the shape described in the present embodiment according to actual splitting needs, as long as positions of the DMDs can be adjusted to ensure that each second beam L2 can cover the effective light modulation area 132 of a matched DMD and achieve regular reflection by the DMD.

Figure 12:
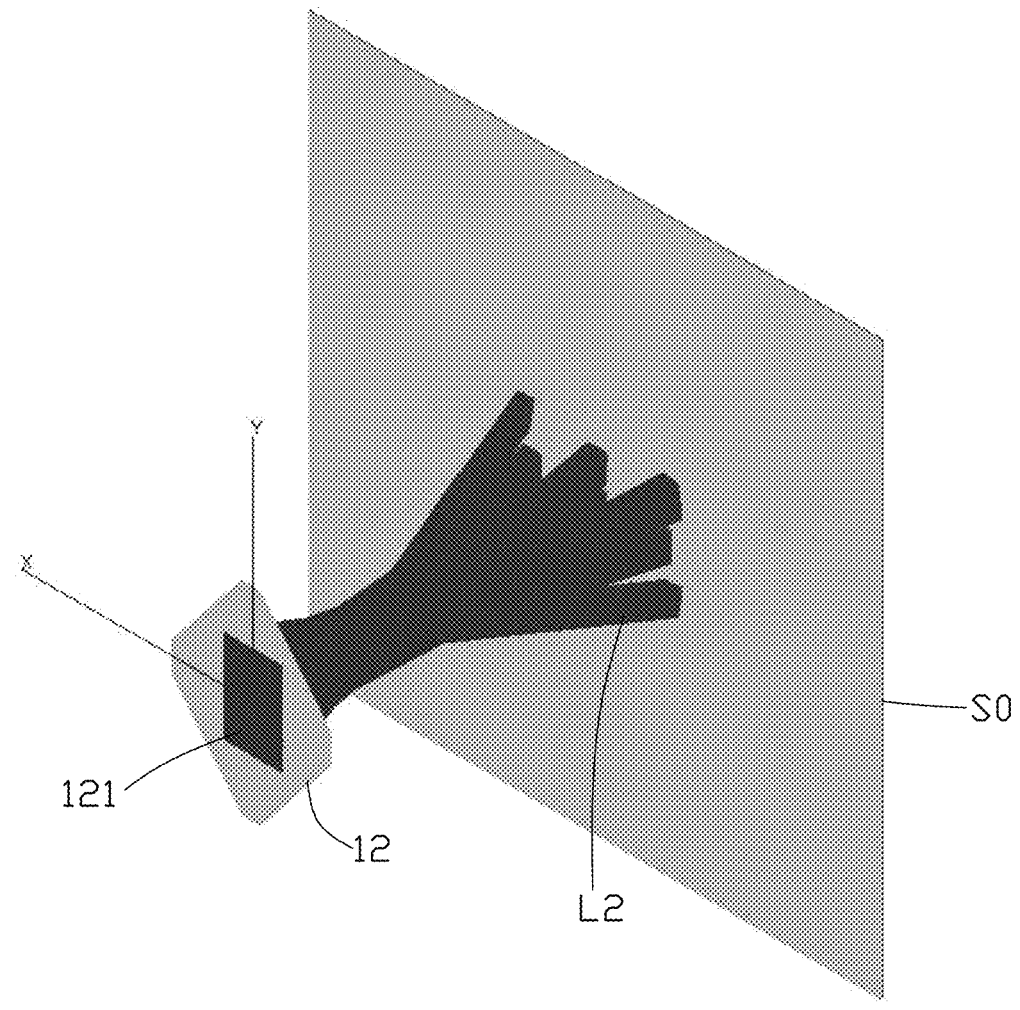
FIG. 12 is a schematic view of a propagation path of second beams from the light guiding element in FIG. 9.
Figure 13:
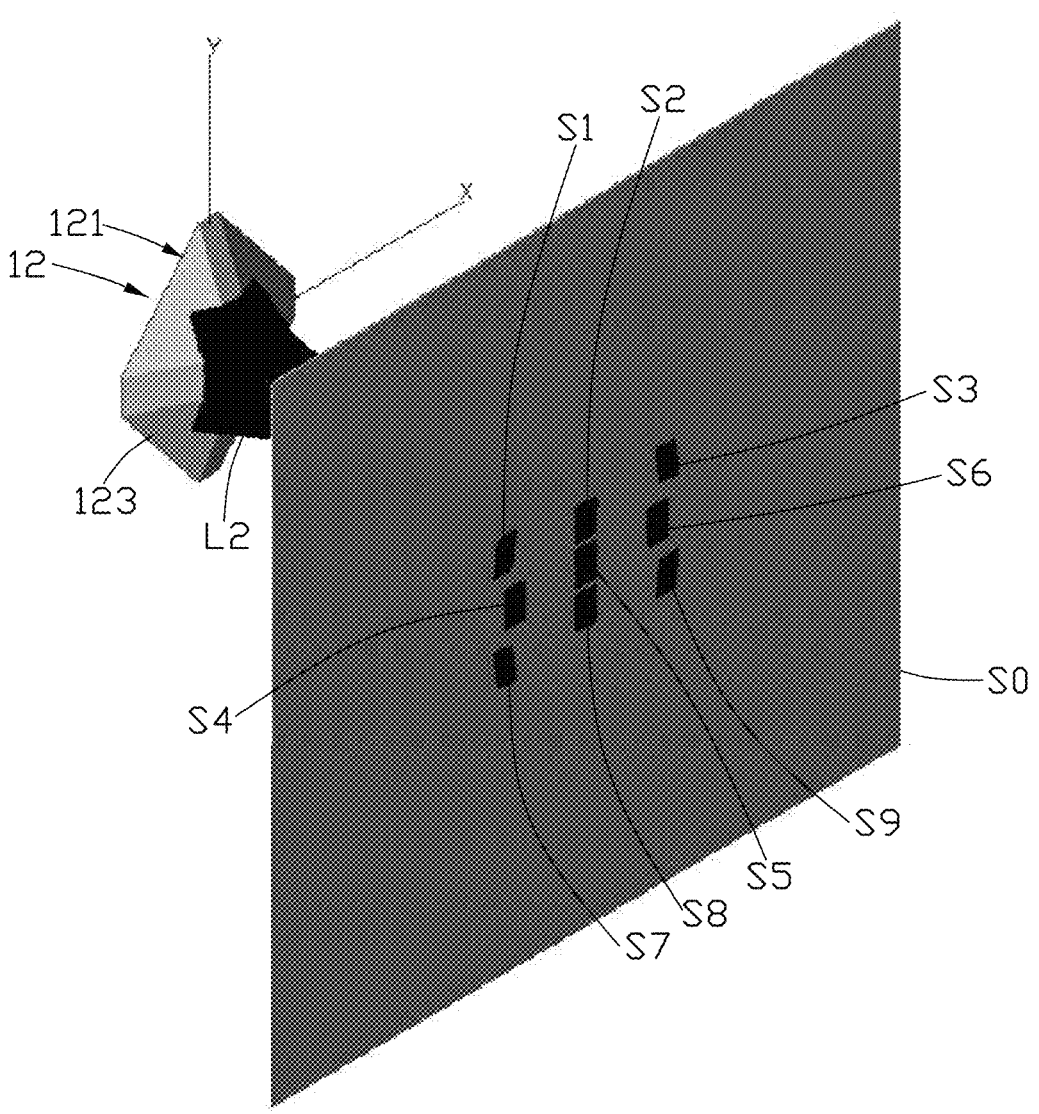
FIG. 13 shows a projection the second beams shown in FIG. 12 on a plane from another perspective.

FIG. 12 shows a propagation path of the second beams L2 from the light guiding element 12 shown in FIG. 9, which satisfies the conditions (1)-(2) above. FIG. 13 shows a projection pattern of the second beams L2 shown in FIG. 12 on a projection plane S0 from another perspective. According to results shown in FIGS. 12 to 13, the propagation path of the second beam L2 is basically the same as that shown in FIGS. 10 and 11. The projection plane S0 is used to represent the plane used by the light modulation module 13 to receive the second beams L2. According to FIG. 13, the nine second beams L2 form projection patterns S1, S2, S3, S4, S5, S6, S7, S8, and S9 on the projection plane S0. An arrangement of the projection patterns S1, S2, S3, S4, S5, S6, S7, S8, and S9 is the same with the arrangement of the light modulators 131 in the light modulation module 13 (referring to FIG. 9), which enables each second beam L2 to be correspondingly projected onto the light modulator 131 by the light guiding element 12.

Referring to FIG. 2, after being regularly reflected by the light modulation module 13, the second beams L2 are once again received and combined by the light guiding element 12 to form the illumination light L3. The illumination light L3 can be guided to the biological sample 20 through the incident surface 121.

The illumination light L3 irradiates the surface of the biological sample 20 to excite biological sample 20 to emit fluorescence light, and the fluorescence light emitted by biological sample 20 is defined as a detection light L4. In this embodiment, the imaging module 14 is used to receive the detection light L4 and obtain a detection image of the biological sample 20 based on the detection light L4.

In this embodiment, the biological sample 20 is excited by the illumination light L3 to generate four different wavelengths of fluorescence lights, that is, the detection light L4 includes four different wavelengths of fluorescence lights. The imaging module 14 includes four imaging channels, each of which is used to receive a fluorescence light of one of the wavelengths (i.e., each imaging channel is used to receive a part of detection light L4). In other embodiments, the imaging module 14 may include other numbers of imaging channels, which are determined by the number of fluorescence wavelengths in the detection light L4. Specifically, each imaging channel corresponds to one wavelength of the fluorescence light. That is, fluorescence light of each wavelength correspondingly gets transmitted onto one single imaging channel.

Each imaging channel includes a filter 141 and a camera 142 arranged sequentially on an optical path of the detection light L4. The filter 141 allows only the fluorescent light of one wavelength (or wavelength band) to pass through and get transmitted onto the camera 142. The camera 142 can generate the detection image based on the fluorescence light received, which can be used to obtain the biological feature of the biological sample 20.

The control portion 15 is electrically connected to the laser device 111 in the light source module 11, each light modulator 131 in the light modulation module 13, and each camera in the imaging module 14, which is configured for controlling switch state of the laser device 111 in the light source module 11, the rotation state ("ON" state or "OFF" state) of the micro mirrors 134 in the light modulator 131, and an operation process of each camera. The control portion 15 is also used to identify the biological feature of the biological sample based on preset algorithms according to the detection image obtained as mentioned above. The control portion 15 can be a computer, a control chipset, or the like.

The biological sample identification device 10 of this embodiment also includes a light guiding device for guiding light (including the first beam L1, the second beams L2, the illumination light L3, and the detection light L4) in a specific way. The light guiding device includes a total internal reflector 161, five lenses 162, four dichroic mirrors 163, and an objective lens 164. The total internal reflector 161 is positioned in both an optical path the first beam L1 and that of the illumination light L3, and configured to guide the first beam to the light guiding element 12, and to guide the illumination light L3 to the biological sample 20 through lens 162, dichroic mirror 163, and the objective lens 164, by expanding, evenly distributing, and transmitting a received light. Each of the other four lenses 162 are positioned between the filter 141 and the camera 142 in a imaging channel, for focusing the fluorescence light onto the camera 142. Each dichroic mirror 163 is used to reflect or transmit received light according to the wavelength of the received light. The objective lens 165 is used to focus the illumination light L3 onto the biological sample 20 (or onto the sequencing chip 30).

The above light guiding devices are only used as examples and are not intended to limit the present disclosure. In other implementations, the above light guiding devices may be replaced by other types of light guiding devices or a combination of a plurality of other light guiding devices that can achieve a same guiding effect on light.

In the biological sample identification device 10 of this embodiment, the light guiding element 12 includes a first exit surface 122 and a plurality of second exit surfaces 123. The light guiding element 12 is used to split the first beam L1 emitted by the light source module 11, so that the first exit surface 122 and each second exit surface 123 respectively emit one of the second beams L2 to project each second beam L2 onto one light modulator 131 in the light modulation module 13. The light modulator 131 is used for regularly reflecting the second beam L2 received, causing each second beam L2 to return to the light guiding element 12 along an original optical path. The light guiding element 12 is used for combining the second beams L2 reflected by the light modulators 131 to form the illumination light L3, and the field of view area of the illumination light L3 is a sum of the field of view areas of the second beams L2. In another embodiment of this disclosure, the field of view area of the illumination light L3 may not be the sum of the field of view areas of the second beams L2, and the field of view area of the illumination light L3 is greater than or equal to the field of view area of any one of second beams L2. When the field of view area of the illumination light L3 is the sum of the field of view areas of the second beams L2, the field of view areas of the second beams L2 can be greatly utilized.

Compared to prior art, the biological sample identification device 10 in this disclosure splits the first beam L1 and combines the second beams L2 by the light guiding element 12, further cooperates with the light modulators 131 to obtain the illumination light L3 with a larger field of view area. In the biological sample identification device 10, the field of view area of the objective lens 164 is usually larger than that of light reflected by one light modulator 131. Therefore, by increasing the number of the light modulators 131, the illumination light L3 with a field of view area several times larger than a field of view area of one second beam L2 is obtained, which is conducive to match the field of view area of the objective lens 164 and making full use of it. The field of view area of the illumination light L3 can be slightly larger, or slightly smaller, or equal to the field of view area of the objective lens 164. When the field of view area of the illumination light L3 is slightly greater than or equal to the field of view area of the objective lens 164, the maximum utilization of the field of view area of the objective lens 164 can be achieved. When the field of view area of the illumination light L3 is slightly smaller than that of the objective lens 164, it is beneficial to avoid waste of illumination light L3 and thus improve a utilization rate of the illumination light L3.

The field of view area of light beam (such as the second beams L2 and the illumination light L3) described in this embodiment can be defined as the spot area formed when the light beam reaches the biological sample 20. The field of view area of the objective 165 is determined by a field angle of the objective 165.

The light source module 11, the light guiding element 12, and the light modulation module 13 can form a field of view stitching system, which can be applied to other optical systems except for super-resolution imaging device 10, such as laser projection or computational lithography. Based on a process of splitting the first beam L1 and combining the second beams L2 by the light guiding element 12 in the field of view stitching system, the light modulation module 13 can include a plurality of light modulators 131, which is conducive to splicing the field of view of the second beams L2 reflected by the light modulators 131, and obtaining the illumination light with a larger field of view to fully utilize the field of view of the objective lens in the optical system.

Referring to FIG. 14, this embodiment also provides a field of view stitching method, which is applied to the field of view stitching system. The field of view stitching method includes the following steps.

In step S11, the light source module emits the first beam towards the incident surface.

In step S12, the first exit surface and the second exit surfaces split the first beam into the plurality of second beams, and the plurality of second beams exit through the first exit surface and the second exit surfaces and propagate along the optical path of the first beam.

In step S13, each of the plurality of second beams is transmitted to one of the plurality of light modulators, each of the plurality of light modulators is controlled to receive one of the plurality of second beams and perform regular reflection, and each of the plurality of second beams covers the effective light modulation area of one of the light modulators.

In step S14, each of the plurality of second beams regularly reflected along the opposite direction of the optical path to enter the light guiding element through the first exit surface and the plurality of second exit surfaces, and the plurality of second beams are combined by the incident surface to form the illuminating light.

The steps S11, S12, S13, and S14 in the above field of view stitching method correspond to operation processes of the light source module 11, the light guiding element 12, and the light modulation module 13 in the field of view stitching system and the operation processes will not be repeated here.

Referring to FIG. 15, this embodiment also provides a biological sample identification method based on super-resolution imaging, which is applied to the biological sample identification device 100 based on super-resolution imaging. The biological sample identification method based on super-resolution imaging applied with the steps in the field of view stitching method. The biological sample identification method based on super-resolution imaging specifically includes the following steps.

In step S21, the light source module emits the first beam towards the incident surface.

In step S22, the first exit surface and the second exit surfaces split the first beam into the plurality of second beams, and the plurality of second beams exit through the first exit surface and the second exit surfaces and propagate along the optical path of the first beam.

In step S23, each of the plurality of second beams is transmitted to one of the plurality of light modulators, each of the plurality of light modulators receives one of the plurality of second beams and perform regular reflection, and each of the plurality of second beams covers the effective light modulation area of one of the light modulators.

In step S24, each of the plurality of second beams reflected regularly enters the light guiding element along the opposite direction of the optical path through the first exit surface and the plurality of second exit surfaces, and the plurality of second beams are combined by the incident surface to form the illuminating light.

In step S25, the illumination light exits from the exiting surface to the biological sample to generate the detection light.

In step S26, the method includes collecting the detection light and generating the detection image based on the detection light.

In step S27, the method includes identifying the biological feature of the biological sample based on the detection image.

The steps S21, S22, S23, S24, S25, S26, and S27 in the biological sample identification method based on super-resolution imaging correspond to operation processes of the light source module 11, the light guide element 12, the light modulation module 13, the imaging module 14, and the control portion 15 in the biological sample identification device 100 based on super-resolution imaging, and the operation processes will not be repeated here.

The above field of view stitching method and the biological sample identification method based on super-resolution imaging can achieve all the beneficial effects of the field of view stitching system and the biological sample identification device based on super-resolution imaging.

Ordinary technicians in the technical field should realize that the above embodiments are only used to illustrate the present disclosure and not to limit the present disclosure. Appropriate changes made to the above embodiments fall within a protection scope of the present disclosure as long as the changes are within a substantive spirit of the present disclosure.

What is claimed is:

1. A field of view stitching system comprising:
a light source module for emitting a first beam;
a light guiding element on an optical path of the first beam and configured to split the first beam into a plurality of second beams, wherein the light guiding element comprises an incident surface positioned corresponding to the light source module, a first exit surface facing and spaced apart from the incident surface, and a plurality of second exit surfaces configured to bend and extend from edges of the first exit surface towards the incident surface, the plurality of second beams configured to exit from the first exit surface and the plurality of second exit surfaces and propagate along the optical path; and a light modulation module comprising a plurality of light modulators, wherein, a number of the plurality of light modulators is the same as a total number of the first exit surface and the plurality of second exit surfaces, each of the plurality of light modulators is configured to receive and regularly reflect one of the plurality of second beams, each of the plurality of light modulators has an effective light modulation area, each of the plurality of second beams is configured to cover the effective light modulation area of one of the light modulators when incident on the light modulator; wherein the light guiding element is further configured for receiving and combining the plurality of second beams reflected by the plurality of light modulators to form an illuminating light to further exit through an exit surface the incident surface.

2. The field of view stitching system of claim 1, wherein one of the plurality of second beams exit from the first exit surface, and other second beams of the plurality of second beams exit from the plurality of second exit surfaces, the first exit surface is connected to the plurality of second exit surfaces, and the plurality of second exit surfaces surround the first exit surface.

3. The field of view stitching system of claim 2, wherein the light guiding element comprises a stage portion and a protrusion portion, the protrusion portion is connected to an end of the stage portion and coaxial with the stage portion, a surface of the protrusion portion comprises the first exit surface and the plurality of second exit surfaces, a surface of the stage portion away from the protrusion portion is the incident surface, and the incident surface is parallel to the first exit surface.

4. The field of view stitching system of claim 3, wherein the first exit surface is polygonal, and a number of sides of the plurality of second exit surfaces is the same as a number of sides of the first exit surface.

5. The field of view stitching system of claim 3, wherein the first exit surface is polygonal, a number of the plurality of second exit surfaces is twice a number of sides of the first exit surface, the second exit surface comprises a plurality of first refraction surfaces and a plurality of second refraction surfaces, with a one-to-one correspondence between the plurality of first refraction surfaces and sides of the first exit surface, and a one-to-one correspondence between the plurality of second refraction surfaces and corners of the plurality of second exit surfaces first exit surface, and each of the plurality of second refraction surfaces is formed between any two adjacent first refraction surfaces.

6. The field of view stitching system of claim 3, wherein the stage portion is in shape of a cylinder with a plurality of arris, and a number of the plurality of arris is the same as a number of the plurality of second exit surfaces.

7. The field of view combination system of claim 1, wherein each of the plurality of light modulators comprises a plurality of micro mirrors in the effective light modulation area, each of the plurality of micro mirrors has a rotation angle α, the effective light modulation area of each of the plurality of light modulators is rectangular with a length L and a width W, a length of each of the plurality of light modulators is X, a width of each of the plurality of light modulators is Y, the plurality of second exit surfaces surround the first exit surface and are axially symmetric around an axis in an X direction and another axis in a Y direction, the X direction is parallel to a length direction of the plurality of light modulators, and the Y direction is parallel to a width direction of the plurality of light modulators, the plurality of light modulators are configured in an array arrangement with a plurality of rows with a same number of the light modulators, having a space ΔX between every adjacent two of the light modulators along the X direction; on a plane formed by the X direction and an optic axis of the light guiding element, a cone angle between the incident surface and the plurality of second exit surfaces corresponding to the plurality of light modulators arranged along the Y direction is «; a refractive index of the light guiding element is n, a distance between the first exit surface and the light modulation module along the optic axis is H, and following condition is satisfied:

$$2H\tan[\alpha(n-1)]=2X+2\Delta X+L.$$

8. The field of view stitching system of claim 7, wherein a distance between adjacent light modulators along the Y direction is ΔY;
    on a plane formed by the optic axis and the Y direction, a cone angle between the plurality of second exit surfaces and the incident surface corresponding to the plurality of light modulators along the Y direction is β, and the following condition is satisfied:

$$2H\tan[\beta(n-1)]=2Y+2\Delta Y+W.$$

9. The field of view stitching system of claim 1, wherein the light source module comprises at least one laser device and at least one beam expanding lens, the at least one beam expanding lens is positioned between the at least one laser device and the light guiding element;
    the at least one laser device is configured to emit the first beam, the at least one beam expanding lens is configured to receive, expand, and collimate the first beam, and a spot area of the first beam after being expanded and collimated by the at least one beam expanding lens is a sum of the effective light modulation area of the plurality of light modulators.

10. The field of view stitching system of claim 1, wherein a field of view area of the illumination light is greater than a field of view area of any one of the plurality of second beams.

11. The field of view stitching system of claim 10, wherein the field of view area of the illumination light is a sum of the field of view areas of the plurality of second beams.

12. A biological sample identification device based on super-resolution imaging, comprising:
    a field of view stitching system, comprising: a light source module for emitting a first beam;
    a light guiding element on an optical path of the first beam and configured to split the first beam into a plurality of second beams, wherein the light guiding element comprises an incident surface positioned corresponding to the light source module, a first exit surface facing and spaced apart from the incident surface, and a plurality of second exit surfaces configured to bend and extend from edges of the first exit surface towards the incident surface, the plurality of second beams configured to exit from the first exit surface and the plurality of second exit surfaces and propagate along the optical path; and
    a light modulation module comprising a plurality of light modulators, wherein a number of the plurality of light modulators is the same as a total number of the first exit surface and the plurality of second exit surfaces, each of the plurality of light modulators is configured to receive and regularly reflect one of the plurality of second beams, each of the plurality of light modulators has an effective light modulation area, each of the plurality of second beams is configured to cover the effective light modulation area of one of the light modulators when incident on the light modulator; wherein the light guiding element is further configured to receive and combine the plurality of second beams reflected to form an illuminating light to further exit through the incident surface and further configured to irradiate a biological sample to cause a detection light;
    an imaging module configured for receiving the detection light and generating a detection image based on the detection light; and a control portion electrically connected to the light source module, the plurality of light modulators, and the imaging module, the control portion configured to control an operation process of the light source module, the plurality of light modulators, and the imaging module, and to identify a biological feature of the biological sample based on the detection image.

13. The biological sample identification device based on super-resolution imaging of claim 12, wherein one of the plurality of second beams exit from the first exit surface, and other second beams of the plurality of second beams exit from the plurality of second exit surfaces, the first exit surface is connected to the plurality of second exit surfaces, and the plurality of second exit surfaces surround the first exit surface.

14. The biological sample identification device based on super-resolution imaging of claim 13, wherein the light guiding element comprises a stage portion and a protrusion portion, the protrusion portion is connected to an end of the stage portion and coaxial with the stage portion, a surface of the protrusion portion comprises the first exit surface and the plurality of second exit surfaces, a surface of the stage portion away from the protrusion portion is the incident surface, and the incident surface is parallel to the first exit surface.

15. The biological sample identification device based on super-resolution imaging of claim 14, wherein the first exit surface is polygonal, and a number of the plurality of second exit surfaces is the same as a number of sides of the first exit surface.

16. The biological sample identification device based on super-resolution imaging of claim 14, wherein the first exit surface is polygonal, a number of the plurality of second exit surfaces is twice a number of sides of the first exit surface, the second exit surface comprises a plurality of first refraction surfaces and a plurality of second refraction surfaces, with a one-to-one correspondence between the plurality of first refraction surfaces and sides of the first exit surface, and a one-to-one correspondence between the plurality of second refraction surfaces and corners of the first exit surface, and each of the plurality of second refraction surfaces is formed between any two adjacent first refraction surfaces.

17. The biological sample identification device based on super-resolution imaging of claim 14, wherein the stage portion is in shape of a cylinder with a plurality of arris, and a number of the plurality of arris is the same as a number of the plurality of second exit surface.

18. The biological sample identification device based on super-resolution imaging of claim 12, wherein each of the plurality of light modulators comprises a plurality of micro mirrors in the effective light modulation area, each of the plurality of micro mirrors has a rotation angle $\alpha$, the effective light modulation area of each of the plurality of light modulators is rectangular with a length L and a width W, a length of each of the plurality of light modulators is X, a width of each of the plurality of light modulators is Y, the plurality of second exit surfaces surround the first exit surface and are axial symmetry along a X direction and another axis in a Y direction, the X direction is parallel to a length direction of the plurality of light modulators, and the Y direction is parallel to a width direction of the plurality of light modulators, the plurality of light modulators are configured in an array arrangement with a plurality of rows with a same number of the light modulators, having a space $\Delta X$ between every adjacent two of the light modulators along the X direction; on a plane formed by the X direction and an optic axis of the light guiding element, a cone angle between the incident surface and the plurality of second exit surfaces corresponding to the plurality of light modulators arranged along the Y direction is $\alpha$; a refractive index of the light guiding element is n, a distance between the first exit surface and the light modulation module along the optic axis is H, and the following condition is satisfied:

$$2H \tan[\alpha(n-1)]=2X+2\Delta X+L.$$

19. The biological sample identification device based on super-resolution imaging of claim 18, wherein a distance between adjacent light modulators along the Y direction is $\Delta Y$;

on a plane formed by the optic axis and the Y direction, a cone angle between the plurality of second exit surfaces and the incident surface corresponding to the plurality of light modulators along the Y direction is $\beta$, and the following condition is satisfied:

$$2H \tan[\beta(n-1)]=2Y+2\Delta Y+W.$$

20. The biological sample identification device based on super-resolution imaging of claim 12, wherein the light source module comprises at least one laser device and at least one beam expanding lens, the at least one beam expanding lens is positioned between the at least one laser device and the light guiding element;

the at least one laser device is configured to emit the first beam, the at least one beam expanding lens is configured to receive, expand, and collimate the first beam, and a spot area of the first beam after being expanded and collimated by the at least one beam expanding lens is a sum of the effective light modulation area of the plurality of light modulators.

21. The biological sample identification device based on super-resolution imaging of claim 12, wherein a field of view area of the illumination light is greater than a field of view area of any one of the plurality of second beams.

22. The biological sample identification device based on super-resolution imaging of claim 21, wherein the field of view area of the illumination light is a sum of the field of view areas of the plurality of second beams.

23. A field of view stitching method applied to a field of view stitching system, wherein the field of view stitching system includes a light source module, a light guiding element, and a light modulation module, the light modulation module is provided with a plurality of light modulators, the light guiding element is provided with an incident surface, a first exit surface facing the incident surface, and a plurality of second exit surfaces bending and extending from edges of the first exit surface towards the incident surface, a number of the plurality of light modulators is the same as a total number of the first exit surface and the plurality of second exit surfaces, and each of the plurality of light modulators has an effective light modulation area; the field of view stitching method comprises:

emitting a first beam towards the incident surface by the light source module;

splitting the first beam into a plurality of second beams by the first exit surface and the plurality of second exit surfaces, and further directing the plurality of second beams to exit from the first exit surface and the plurality of second exit surfaces and propagate along an optical path of the first beam;

transmitting each of the plurality of second beams to one of the plurality of light modulators, controlling each of the plurality of light modulators to receive and regularly reflect one of the plurality of second beams, and with each of the plurality of second beams covering the effective light modulation area of the light modulator; and forming an illumination light on the incident surface by a combination of the plurality of second beams which are regularly reflected to the light guiding element along an opposite direction of the optical path and pass through the first exit surface and the plurality of second exit surfaces.

24. The field of view stitching method of claim 23, wherein each of the plurality of light modulators is provided with a plurality of micro mirrors in the effective light modulation area, a rotatable angle of each of the plurality of micro mirrors is $\alpha$, the effective light modulation area is rectangular with a length of L and a width of W, each of the plurality of light modulators has a length of X and a width of Y, the plurality of second exit surfaces are symmetrically distributed about the first exit surface and around an axis in an X direction and another axis in a Y direction, the X direction is parallel to a length direction of the plurality of light modulators, the Y direction is parallel to a width direction of the plurality of light modulators, the plurality of light modulators are arranged in a symmetrical array along the X direction and the Y direction; on a plane formed by an optic axis of the light guiding element and the X direction, a cone angle between the incident surface and the plurality of second exit surfaces corresponding to the plurality of light modulators arranged along the Y direction is $\alpha$;

the field of view stitching method further includes:

adjusting space between each adjacent two of the light modulators to generate the illumination light, including: adjusting the space between each adjacent two of the light modulators along the X direction, and adjusting a distance H between the first exit surface and the light modulation module along the optic axis; the space between each adjacent two light modulators along the Y direction is $\Delta X$, the cone angle $\alpha$ equals the rotation angle $\alpha$, and a condition of $2H \tan[\alpha(n-1)]=2X+2\Delta X+L$ is satisfied.

25. The field of view stitching method of claim 24, wherein adjusting space between each adjacent two of the light modulators to generate the illumination light further comprises:

adjusting the space between each adjacent two of the light modulators along the Y direction according to a condition of $2H \tan[\beta(n-1)]=2Y+2\Delta Y+W$, wherein the space between each adjacent two of the light modulators along the Y direction is $\Delta Y$; and on a plane formed by an optic axis and the Y direction, a cone angle between the incident surface and the plurality of second exit surfaces corresponding to the plurality of light modulators arranged along the Y direction is $\beta$.

26. A biological sample identification method based on super-resolution imaging and is applied to the biological sample identification device of claim 12, the biological sample identification device is provided with a field of view stitching system including a light source module, a light guiding element, and a light modulation module, the light modulation module is provided with a plurality of light modulators, the light guiding element is provided with an incident surface positioned corresponding to the light source module, a first exit surface facing and positioned apart from the incident surface, and a plurality of second exit surfaces bending and extending from edges of the first exit surface towards the incident surface, a number of the plurality of light modulators is the same as a total number of the first exit surface and the plurality of second exit surfaces, and each of the plurality of light modulators has an effective light modulation area; the biological sample identification method based on super-resolution imaging comprises:

emitting a first beam towards the incident surface by the light source module;

splitting the first beam into a plurality of second beams by the first exit surface and the plurality of second exit surfaces, and further directing the plurality of second beams to exit from the first exit surface and the plurality of second exit surfaces and propagate along an optical path of the first beam;

transmitting each of the plurality of second beams to one of the plurality of light modulators, controlling each of the plurality of light modulators to receive and regularly reflect one of the plurality of second beams, and with each of the plurality of second beams covering the effective light modulation area of the light modulator;

forming an illumination light on the incident surface by a combination of the plurality of second beams which are regularly reflected to the light guiding element along an opposite direction of the optical path and pass through the first exit surface and the plurality of second exit surfaces;

irradiating a biological sample with the illumination light through the incident surface to generate a detection light from the biological sample;

collecting the detection light and generating a detection image based on the detection light; and identifying a biological feature of the biological sample based on the detection image.

27. The biological sample identification method based on super-resolution imaging of claim 26, wherein each of the plurality of light modulators is provided with a plurality of micro mirrors in the effective light modulation area, a rotatable angle of each of the plurality of micro mirrors is $\alpha$, the effective light modulation area is rectangular with a length of L and a width of W, each of the plurality of light modulators has a length of X and a width of Y, the plurality of second exit surfaces are symmetrically distributed about the first exit surface and around an axis in an X direction and another axis in a Y direction, the X direction is parallel to a length direction of the plurality of light modulators, the Y direction is parallel to a width direction of the plurality of light modulators, the plurality of light modulators are arranged in a symmetrical array along the X direction and the Y direction; on a plane formed by an optic axis of the light guiding element and the X direction, a cone angle between the incident surface and the plurality of second exit surfaces corresponding to the plurality of light modulators arranged along the Y direction is $\alpha$;

the field of view stitching method further includes:

adjusting space between each adjacent two of the light modulators to generate the illumination light, including: adjusting the space between each adjacent two of the light modulators along the X direction, and adjusting a distance H between the first exit surface and the light modulation module along the optic axis; wherein the space between each adjacent light modulators along the Y direction is $\Delta X$, the cone angle $\alpha$ equals the rotation angle $\alpha$, and a condition of $2H \tan[\alpha(n-1)]=2X+2\Delta X+L$ is satisfied.

28. The biological sample identification method based on super-resolution imaging of claim 27, wherein adjusting space between each adjacent two of the light modulators to generate the illumination light further comprises:

adjusting the space between each adjacent two of the light modulators along the Y direction according to a condition $2H \tan[\beta(n-1)]=2Y+2\Delta Y+W$, wherein the space between each adjacent two of the light modulators along the Y direction is $\Delta Y$; and on a plane formed by an optic axis and the Y direction, a cone angle between the incident surface and the plurality of second exit surfaces corresponding to the plurality of light modulators arranged along the Y direction is $\beta$.

* * * * *